United States Patent
Nordhoff et al.

(10) Patent No.: US 8,252,120 B2
(45) Date of Patent: Aug. 28, 2012

(54) WASHING APPARATUS, A METHOD OF PURIFYING A WASH MATERIAL AND USE OF THE WASHING APPARATUS

(75) Inventors: Stefan Nordhoff, Recklinghausen (DE); Torsten Balduf, Houston, TX (US); Joachim Deinken, Dorsten (DE); Joachim Pohlisch, Gelnhausen (DE); Axel Hengstermann, Senden (DE)

(73) Assignee: Evonik Stockhausen GmbH, Krefeld (DE)

( * ) Notice: Subject to any disclaimer, the term of this patent is extended or adjusted under 35 U.S.C. 154(b) by 1242 days.

(21) Appl. No.: 10/527,519

(22) PCT Filed: Sep. 15, 2003

(86) PCT No.: PCT/EP03/10251
§ 371 (c)(1),
(2), (4) Date: Aug. 30, 2005

(87) PCT Pub. No.: WO2004/026429
PCT Pub. Date: Apr. 1, 2004

(65) Prior Publication Data
US 2006/0013748 A1     Jan. 19, 2006

(30) Foreign Application Priority Data
Sep. 13, 2002 (DE) .................. 102 42 746

(51) Int. Cl.
*B01D 9/00* (2006.01)
*B08B 7/04* (2006.01)

(52) U.S. Cl. ....... 134/13; 422/245.1; 422/105; 210/175; 210/109; 23/295 R

(58) Field of Classification Search .................. 422/188; 210/767, 175, 189
See application file for complete search history.

(56) References Cited

U.S. PATENT DOCUMENTS

| 2,540,083 A | 2/1951 | Arnold |
| RE24,038 E | 7/1955 | Arnold |
| 2,770,533 A * | 11/1956 | Kahmann et al. ............. 422/105 |

(Continued)

FOREIGN PATENT DOCUMENTS

DE     1 947 251     5/1970

(Continued)

OTHER PUBLICATIONS

Jansens et al. The purification process in hydraulic packed-bed wash columns. Chemical Engineering science, vol. 50, No. 17 (1995) pp. 2717-2729.*

(Continued)

*Primary Examiner* — Vickie Kim
*Assistant Examiner* — Katherine Zalasky
(74) *Attorney, Agent, or Firm* — Smith Moore Leatherwood LLP; Philip P. McCann

(57) ABSTRACT

The invention relates to a washing apparatus, including a First Region (1) to which a wash material (4) is supplied, a Second Region (2), in which the wash material (4) is washed, and a Third Region (3), in which the wash material (4) is melted and a flow resistance (6), which is provided between the Second Region (2) and the Third Region (3), a purification apparatus, a synthesis device, a method for purifying a wash material, and the use of a washing apparatus or a purification apparatus for purifying and then using the target product obtained by the purification.

28 Claims, 6 Drawing Sheets

U.S. PATENT DOCUMENTS

| | | | |
|---|---|---|---|
| 3,637,081 A * | 1/1972 | Bradley | 210/110 |
| 3,645,699 A | 2/1972 | Brodie | |
| 3,652,230 A * | 3/1972 | Girling | 422/251 |
| 3,777,892 A | 12/1973 | Thijssen et al. | |
| 3,801,285 A * | 4/1974 | Meisenburg et al. | 422/254 |
| 3,872,009 A | 3/1975 | Thijssen | |
| 4,188,797 A | 2/1980 | Thijssen et al. | |
| 4,309,878 A | 1/1982 | Brennan | |
| 4,332,140 A * | 6/1982 | Thijssen et al. | 62/123 |
| 4,332,599 A | 6/1982 | Thijssen et al. | |
| 4,383,121 A | 5/1983 | Sugamiya et al. | |
| 4,418,030 A * | 11/1983 | Muller et al. | 264/142 |
| 4,475,355 A | 10/1984 | Thijssen et al. | |
| 4,652,675 A | 3/1987 | Goorden et al. | |
| 4,705,624 A | 11/1987 | Thijssen | |
| 4,734,102 A | 3/1988 | Thijssen et al. | |
| 4,735,781 A | 4/1988 | Thijssen et al. | |
| 4,762,622 A | 8/1988 | Thijssen | |
| 4,830,645 A * | 5/1989 | Ghodsizadeh et al. | 62/541 |
| 4,840,737 A | 6/1989 | Henriquez | |
| 5,102,544 A | 4/1992 | Roodenrijs | |
| 5,406,641 A * | 4/1995 | Bigley et al. | 385/141 |
| 6,241,101 B1 | 6/2001 | Roodenrijs | |
| 6,541,665 B1 * | 4/2003 | Bastiaensen et al. | 562/600 |
| 7,323,016 B2 * | 1/2008 | Heilek et al. | 23/295 R |
| 2003/0060661 A1 | 3/2003 | Eck et al. | |
| 2003/0175159 A1 | 9/2003 | Heilek et al. | |
| 2004/0116741 A1 | 6/2004 | Nordhoff et al. | |
| 2005/0006318 A1 | 1/2005 | Jansens et al. | |

FOREIGN PATENT DOCUMENTS

| | | |
|---|---|---|
| DE | 2 122 339 | 7/1972 |
| DE | 2 347 948 | 4/1974 |
| DE | 28 00 540 A1 | 7/1978 |
| DE | 3 786 471 | 8/1993 |
| DE | 100 36 880 A1 | 2/2002 |
| DE | 100 36 881 A1 | 2/2002 |
| DE | 100 39 025 A1 | 2/2002 |
| EP | 0 097 405 B1 | 1/1984 |
| EP | 0 175 401 | 3/1986 |
| EP | 0 193 226 A1 | 9/1986 |
| EP | 0 235 857 B1 | 9/1987 |
| EP | 0 373 720 A1 | 6/1990 |
| EP | 0 920 894 A1 | 6/1999 |
| EP | 1 295 628 A1 | 3/2003 |
| GB | 2 023 564 A | 1/1980 |
| WO | WO 02/09839 A1 | 2/2002 |
| WO | WO 02/055469 A1 | 7/2002 |

OTHER PUBLICATIONS

International Search Report mailed on Feb. 4, 2004 in connection with PCT/EP03/10251.

Gerard F. Arkenbout, Melt Crystallization Technology, book, 1995, pp. 1-4, Technomic Publishing Company, Inc. Lancaster, Pennsylvania, U.S.A.

Hydraulic Wash Columns Solid-Liquid Separation in Melt Crystallization, book, 2000, pp. 1-5, Universal Press Science Publishers, The Netherlands.

Siegbert Rittner and Rudolf Steiner, Die Schmelzkristallisation von organischen Stoffen und ihre groβtechnische Anwendung, book, 1985, pp. 1-12, VCH Verlagsgesellschaft mbH, Weinheim.

Georg Wellinghoff and Klaus Wintermantel, Schmelzkristallisation-theoretische Voraussetzungen und technische Grenzen, symposium, 1991, pp. 1-9.

L. Van Oord-Knol, O.S.L. Bruinsma, and P.J. Jansens, Effect of Compressibility on Performance of Hydraulic Wash Columns, journal, Jul. 2002, pp. 1478-1487, vol. 48, No. 7, AIChE Journal.

P.J. Jansens, O.S.L. Bruinsma, G.M. Van Rosmalen, and R. De Goede, A General Control Strategy for Hydraulic Packed Bed Wash Columns, journal, Sep. 1994, pp. 695-702, vol. 75, Part A, Trans IchemE.

* cited by examiner

WASHING APPARATUS, A METHOD OF PURIFYING A WASH MATERIAL AND USE OF THE WASHING APPARATUS

This application is a national stage application under 35 U.S.C. 371 of international application no. PCT/EP2003/010251 filed Sep. 15, 2003, which is based on German Application no. DE 102 42 746.1 filed on Sep. 13, 2002, and claims priority thereto.

BACKGROUND OF THE PRESENT INVENTION

The present invention relates to a washing apparatus, to a purification apparatus, to a synthesis apparatus, to a method of purifying a wash material, and to the use of a washing apparatus or a purification apparatus for purification and, finally, to the use of the target product obtained by the purification.

Ever higher demands are being made of the purity of products produced in the chemical industry. This is true especially for so-called 'fine chemicals' or pharmaceutical products, which are produced in relatively small amounts. It has likewise been possible, relatively recently, for the trend towards ever higher purity requirements also to be seen in the case of chemicals that are produced in very large amounts. These substances are, for the most part, starting materials that are used in the further synthesis of mass-produced polymers. In this context there may be mentioned, for example, acrylic acid, methacrylic acid, styrene, acrylamide, caprolactam, naphthalene, or phenol. The high purity requirements are applicable especially when the products produced from those starting materials are used in the medical, food or hygiene sectors. By way of example of applications in the medical and hygiene sectors there may be mentioned absorbent polymers based substantially on partially neutralised cross-linked polyacrylic acids, which are used both in the medical and the hygiene sectors in the form of wound dressings or diapers, respectively, for absorbing aqueous body fluids. In the food sector, for example, flocculants based on acrylic acid or acrylamide or both are used in drinking-water treatment.

Another reason for the purity requirements applied to starting materials for polymerisation processes is that the polymerisation processes proceed in a substantially more controlled manner if the monomers used are present in a high degree of purity. It is possible, by that means, for the molecular weights and molecular weight distributions, which are crucial to the properties of the polymers synthesised from the monomers, to be better controlled.

A further area wherein high purity requirements are applied on an industrial scale is the field of waste-water treatment. The fact that organic solvents are increasingly being replaced by water or aqueous solvents in technical synthesis is resulting in ever greater amounts of waste water being produced from synthesis processes. However, the rules of environmental protection require that the products and by-products of the synthesis in question wherein water has been used as solvent be removed as completely as possible from the waste water.

In the food sector, the requirements applied to the purity of products intended for consumption are also ever increasing. This is true especially in the case of concentrate production. Also, for that purpose, there is a great need for economical concentration processes that are not detrimental to the food.

Likewise, because of the further technical development of heating systems, jet engines and internal combustion engines, the use of ever purer fuels is necessary for performance and exhaust gas optimisation.

However, when a chemical compound is synthesised or when a substance is obtained from natural sources, the desired substance is usually not in the form of a pure product. On the contrary, when carrying out synthesis or when obtaining a substance from natural sources, there is produced a mixture of compounds, of which part constitutes the desired substance, together with impurities such as solvents, starting materials and by-products or undesirable isomers. In order to separate off the desired substance from the impurities, distillative separation methods are frequently used on an industrial scale; however, these are associated with high energy use and, in the case of thermally sensitive and usually reactive end products, result in a lowering of the yield, because the desired products react further, owing to the relatively severe thermal conditions.

When the desired substance is a compound which can be crystallised and is present in a liquid mixture of compounds after the synthesis process, melt crystallisation is to be recommended as a very largely gentle method of purifying the desired substances, that is to say of separating out the substance from the liquid mixture of compounds, often referred to as the "feed", in which further by-products are present in dissolved or liquid form. Thereby, the desired compound is crystallised out from the liquid that is referred to as the mother liquor, in the form of a solid, which is separated and re-melted. The melt is then taken off in the form of a pure product.

Customary methods of crystallisation known from the prior art are static and dynamic layer crystallisation, in which the compound to be isolated is precipitated on stationary cooled surfaces, or suspension crystallisation, which is based on the growth of crystals in a suspension. Suspension crystallisation has the advantage over layer crystallisation that it can be carried out in a continuous process. In addition, the purity of the crystals is generally very high because of their comparatively slow rate of growth. However, despite the slow rate of growth, a high product throughput rate can be achieved using suspension crystallisation because, for crystallisation in solution, a comparatively large area, namely the entire surface area of all the individual particles, is available for crystal growth. Suspension crystallisation consequently represents a very effective and economical method of achieving high purity levels in a target product.

Because of the relatively slow growth of the crystals, compared to layer crystallisation, the impurities present in the liquid are to a very large extent not incorporated into the crystal lattice and remain behind in the mother liquor. Even in a single-stage crystallisation process, high-purity crystals of the desired compound are generally obtained.

A further step that is important for the purity of the end product is the separation of the crystals present in the suspension from the other, liquid constituents of the suspension, which for the most part comprise impurities and the non-crystallised portions of the mixture to be purified. That separation is usually performed by means of a solid/liquid separation process. That separation may proceed in one or more stages, wherein at least in the final stage a so-called washing column is usually used as a washing apparatus. In such a washing apparatus, a suspension of crystals produced in a crystalliser is introduced and the suspension of crystals is compacted to form a crystal bed. A washing liquid, preferably the melt comprising the melted crystals themselves, is passed through that crystal bed in a contraflow direction.

Various methods are used for formation of the compact crystal bed. For example, U.S. Re. 24,038 discloses a gravimetrically operating washing column, wherein a crystal suspension is introduced in an upper region of the washing column and the crystal bed forms by virtue of a sedimentation process. In such columns there is, however, a risk that, in the course of the sedimentation process, vertical channels will form in which back-mixing of the mother liquor or crystal suspension with the washing liquid occurs.

As DE OS 1947251 discloses, gravimetrically operating washing columns have been equipped with a stirring mechanism, at least over part of their height, which prevents the formation of vertical liquid channels in the crystal bed. Such stirring mechanisms are, however, associated with the disadvantage that, because of the stirring movement, swirling-up of the crystal bed occurs, which has a disadvantageous effect on the separation performance of the washing apparatus.

Such stirring mechanisms are not required in the case of hydraulic or mechanical washing columns. For example, EP 0 920 894 A1 discloses a hydraulic washing column in which the suspension is conveyed under pressure into a pressure-tight housing and, as a result of the delivery pressure, forms a compacted crystal bed. The pressure is produced in EP 0 920 894 A1 by means of a semi-permeable piston, which is permeable to the liquid phase of the crystal suspension. In DE OS 28 00 540, a rotating conveying element, which is of helical construction, is used as a means of compacting the crystals in order to form the crystal bed.

In order to break-up again the crystals compacted in the crystal bed for supplying them to the region in which the crystals are melted, DE 100 39 025 A1 suggests a rotating removal tool which is arranged opposite the build-up face and which is generally in the form of a rotor blade or scraper.

It is common to the previously described movable means of conveying and compacting the crystals into a crystal bed and of separating off the crystals that they result in a non-homogeneous crystal bed. In addition to the significant costs incurred in incorporating such moving parts into the washing columns, a considerable outlay on maintenance is necessary. Maintenance of the moving parts in the washing column regularly results in operation of the washing column having to be suspended and the parts having to be dismantled, cleaned, repaired or replaced. A further disadvantage of moving parts in the washing column occurs especially during the purification of reactive substances. For example, when purifying acrylic acid, undesirable spontaneous polymerisation often occurs in the region of the seals of the shafts of the movable parts, resulting in operation of the washing column having to be suspended, in the polymers formed having to be removed and in the moving part having to be dismantled, repaired or replaced.

Concerning this problem a washing column is known from DE 37 86 471 T2, which doesn't have any movable parts in the region of the crystal bed. Furthermore, DE 37 86 471 T2 discloses different approaches to reduce or even to avoid plugging or blocking of the inlet opening. However, these methods do not take into account the complex fluidic conditions prevailing in the crystal bed and in the crystal suspension as well as in the region of transition between crystal suspension and crystal bed. These conditions are described in *Effect of Compressibility on Performance of Hydraulic Wash Columns*, L. van Oord-Knol, O. S. L. Bruinsma, P. J. Jansen, AIChE Journal, July 2002, Col. 48, No. 7, pages 1478 et seqq., and in *A general Control Strategy For Hydraulic Packed Bed Wash Columns*, P. J. Jansens, O. S. L. Bruinsma, G. M. van Rosmalen, R. de Goede, Trans IchemE, Vol. 72, Part A, September 1994, pages 695 et seqq., as being directed to the safe operation of washing columns.

BRIEF SUMMARY OF THE PRESENT INVENTION

In general terms, the present invention is accordingly based on the problem of mitigating or overcoming the disadvantages arising out of the prior art.

In particular, one of the problems of the invention is to make available a washing apparatus that can be produced as economically and simply as possible whilst providing suitable separation performance.

Furthermore, one of the problems of the invention is to make available a washing column, which can easily be subjected to an up scaling for large-scale industrial use.

A further problem of the invention is to provide a washing column that has a relatively long service life, which especially will not be interrupted by out-of-service periods caused by excessively frequent repair work.

In addition, one of the problems of the invention is to make available a method of purifying a wash material, which method will allow operation that is as continuous and interruption-free as possible whilst providing suitable separation performance and will accordingly be highly suitable for large-scale industrial use.

The afore-mentioned problems are solved firstly by the subject matter of the main claims herein below and sub-combinations resulting from the subordinate claims.

Furthermore, the afore-mentioned problems are solved by means of a washing apparatus comprising
  a First Region, to which a wash material is supplied,
  a Second Region, in which the wash material is washed, and
  a Third Region, in which the wash material is melted, and also
  a flow resistance provided between the Second Region and the the Third Region.

Furthermore, the invention relates to a washing apparatus comprising
  a First Region, to which a wash material is supplied,
  a Second Region, in which the wash material is washed, and
  a Third Region, in which the wash material is melted, and also
  a flow resistance provided between the Second Region and the the Third Region,
wherein the Second Region is at least partially in the form of a column and wherein this column has a diameter of at least about 300 mm, preferably about 700 mm and more preferably about 1000 mm. Generally the diameter is limited to about 8000 mm.

Due to this dimensioning of the Second Region the complex fluid mechanic of the wash material is taken into account advantageously.

DETAILED DESCRIPTION OF THE INVENTION

Figure 1:
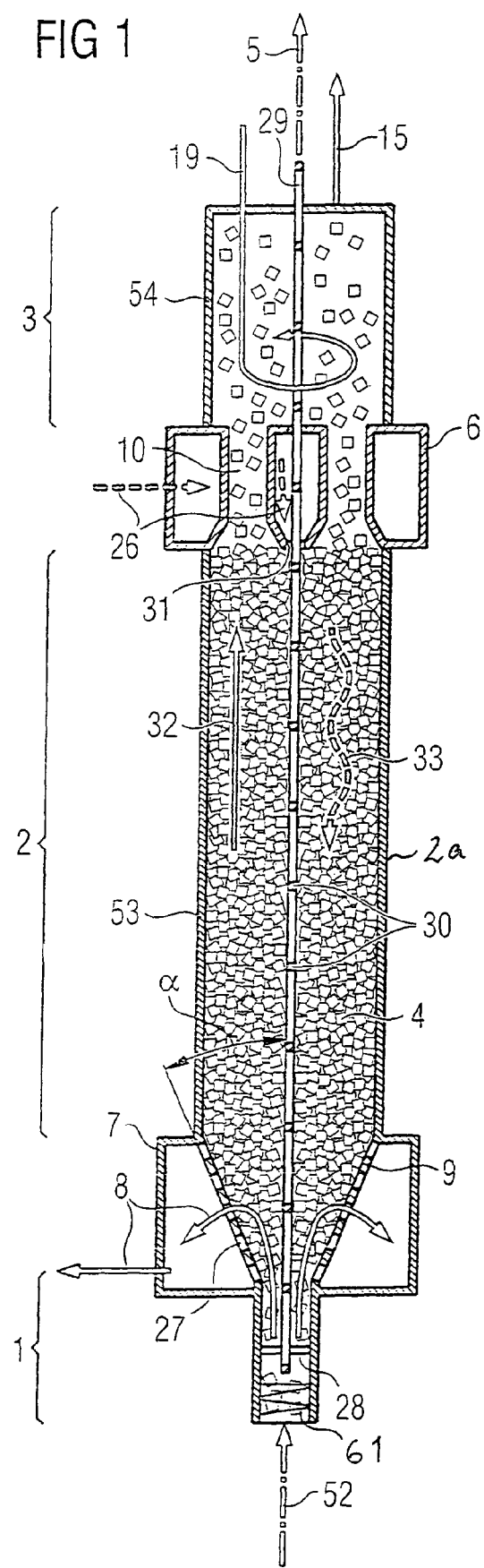
FIG. 1 is a cross-section, in diagrammatic form, through a washing apparatus according to the present invention.

In an embodiment of the washing apparatus according to the invention, it is preferred that the flow resistance is arranged non-rotatable about a central longitudinal axis of the Second Region. In addition, it is preferred that the flow resistance is arranged in a stationary position between the Second Region and the Third Region. It is especially preferred that the flow resistance is in a stationary position between the Second Region and the Third Region being fixedly connected to those Regions.

In accordance with the invention, a crystal suspension is preferred as the wash material. Such a crystal suspension consists of, on the one hand, crystals and, on the other hand, a liquid phase. It is preferred that the crystals consist of at least 50% by weight, preferably at least about 75% by weight, more preferably at least about 95% by weight and even more preferably at least about 99% by weight, and most preferably at least about 99.9% by weight, of a single target product. In principle, the washing apparatus according to the invention can be used for concentrating and for solid/liquid separation. Thereby, the target product may be, on the one hand, the liquid produced during the solid/liquid separation or, on the other hand, a crystallizable solid produced during the concentration. In general terms, target products may be foods, monomers, fuels, solvents, or water from waste-water treatment, or isomers, diastereomers or enantiomers.

As foods, drinks are preferred. As monomers, acrylic acid, methacrylic acid, styrene, methyl methacrylate, butyl acrylate, benzoic acid, bisphenol A, caprolactam, fatty acids, monochloroacetic acid, methyl diisocyanate, toluylene diisocyanate, naphthalene, paraffin, p-, o- or m-dichlorobenzene, p-xylene, phthalide or derivatives of each of those or salts of each of those are preferred. As fuels, hydrazine or diesel is preferred.

Monomeric target products are preferably organic compounds containing from two to 20 carbon atoms and at least one double bond, or water. As organic compounds containing from two to 20 carbon atoms and at least one double bond there may be mentioned styrene, α-methylstyrene, acrylic acid, methacrylic acid, methyl methacrylate and butyl acrylate, whereby acrylic acid, methacrylic acid and methyl methacrylate are preferred and whereby acrylic acid is especially preferred. Where the target product forming the crystals is water, it is especially preferred to use water, which is present as solvent in organic syntheses and which is to be separated off from the main and subsidiary products of those organic syntheses. In that context, mention should be made especially of syntheses of organic compounds containing at least one double bond, preferably acrylic acid, methacrylic acid, acrolein or methacrylate, whereby the syntheses of acrolein or acrylic acid is especially preferred.

When the wash material is present as a mixture of a solid phase and a liquid phase as in the example of the crystal suspension, it is preferred for the solid phase formed by the crystals to be present in a proportion in the range from about 10 to about 80% by weight, preferably from about 15 to about 60% by weight and even more preferably from about 20 to about 40% by weight, in each case based on the total wash material or the total crystal suspension. The wash material also comprises a liquid phase. In the upper portion of the Second Region, the liquid phase mainly comprises a washing liquid originating from the melted crystals. In the lower portion of the Second Region, preferably in the region of the solid/liquid separating device, the liquid phase predominately comprises the mother liquor originating from the formation of crystals in a crystal-producer, which liquor can be taken off by means of the solid/liquid separating device.

Furthermore, it is preferred that the wash material, preferably the crystal suspension, has a viscosity of <250 mPas, preferably equal to or less than about 100 mPas and especially equal to or less than about 50 mPas, determined in accordance with DIN 53019 ISO/ISO 3219.

When the wash material is present in the form of a crystal suspension, it is preferred that the crystals have an average diameter of not more than about 1500 µm, preferably in the range from about 50 to about 1000 µm, more preferably in the range from about 75 to about 500 µm and even more preferably in the range from about t100 to about 250 µm. The average diameter is determined using 500 crystals randomly selected from the crystal suspension. The size of a crystal is the average of the greatest length of a crystal and the diameter of the crystal in question, measured at right angles to the greatest length in the middle thereof. For the purpose of determining the length and diameter, there is used an image analysis system consisting of a light microscope with a connected CCD camera and a PC evaluation unit, with a PC program from the company Soft Imaging Systems (SIS, V3.1) being used.

Furthermore, it is preferred for the washing apparatus according to the present invention that it is possible to reach, at least in the Second Region, a pressure in the range from about 0.1 to about 30 bar, preferably from about 0.5 to about 10 bar and especially from about 1.5 to about 7 bar. Furthermore, it is preferred, that the aforementioned pressure is higher than the pressure on the side of filter facing away from the wash material.

For example in the case of a crystal suspension comprising acrylic acid, the concentration of acrylic acid in the crystals is accordingly at least about 90% by weight, preferably at least about 95% by weight and especially at least about 98% by weight and even more preferably at least about 99% by weight, in each case based on the crystals.

It is especially preferred that the concentration of the melted target product in the liquid phase in the region of the flow resistance is higher in comparison to that in that region of the Second Region which is relatively remote from the flow resistance.

When treating waste water from acrylic acid or acrolein synthesis, preferably from acrolein synthesis, the water crystals forming the crystal suspension consist of at least about 90% by weight, preferably at least about 99% by weight, and especially at least about 99.9% by weight, water, in each case based on the crystals.

In the washing apparatus according to the invention, it is preferred for the First Region, to which a wash material is supplied, to be in the form of an opening, to which there is connected preferably a pipe-like line, which is in communication with at least one wash material conveying means, which is preferably located outside the washing apparatus. Preferably, a plurality of conveying apparatuses are redundantly used for the wash material. This is recommended especially when the wash material comprises reactive compounds. As a result it is possible for operation of the washing apparatus according to the invention to be continued if one or more conveying apparatuses fail, for example as a result of undesirable spontaneous polymerisation of those reactive compounds. Repair of the failed conveying apparatus can be carried out simply and conveniently because the conveying apparatus is located outside the washing apparatus.

As conveying apparatus for the washing apparatus according to the invention there comes into consideration any conveying apparatus that the person skilled in the art considers suitable. Especially preferred are conveying apparatuses that subject the wash material to a minimum of mechanical stress; in particular, a low degree of shear on the wash material is advantageous. In addition, the conveying devices should, as a result of operation that is as free of pulsation as possible, give rise to as little disruption of the crystal bed as possible. "Free of pulsation" means that the pressure of the conveying material at the outlet of the conveying means fluctuates about not less than about 0.5 bar. Against that background, continuously operating spiral conveyor pumps and rotary piston pumps, centrifugal pumps, preferably having a gap width that is as large as possible, preferably at least twice the average crystal diameter, or multi-piston membrane pumps are preferred over discontinuously operating reciprocating piston pumps, whereby spiral conveyor pumps are especially preferred. Therefore, in the washing apparatus according to the invention a conveying means, which is free of pulsation, is provided upstream of the First Region or at least partially in the First Region, wherein the conveying means free of pulsation has preferably a conveying spiral.

The Second Region of the washing apparatus according to the invention, in which the wash material is washed, is, in general terms, so constructed and arranged that the wash material can move within that Region with flow that is very substantially laminar, being very substantially free from non-homogeneities.

During operation of the washing apparatus according to the invention, it is preferred that no build-up front is present in the entire Second Region. The build-up front accordingly refers to the transition from the suspension to the crystal bed and is characterised by a relatively abrupt increase in the crystal content in the suspension. In the operation of the washing apparatus according to the invention, it is furthermore preferred that the build-up front is present in the First Region, preferably above the conveying parts of the conveying apparatus.

Furthermore, it is preferred that, in the case of a Second Region constructed in the form of a pipe, the length of the pipe is not more than about 10 times greater, preferably not more than 5 times greater and especially not more than about 1 time greater, than the cross-section of the pipe used in the Second Region.

The Third Region of the washing apparatus according to the invention, in which the wash material is melted, is preferably so constructed that no regions of pronounced overheating, as a result of which overheating undesirable reactions of reactive compounds present in the wash material may occur, are formed. Like the Second Region, the Third Region of the apparatus according to the invention is also preferably constructed in the form of a pipe. In an embodiment of the Third Region, heating elements are located on the wall of the Third Region. According to another embodiment of the Third Region, heating elements are located within the Third Region. Furthermore, combinations of those two embodiments are possible. According to another embodiment of the washing column according to the invention, a heat exchanger for melting is located, instead or in addition, outside the Third Region. In this case, the heating of the Third Region is achieved by return of the melted target product. This heat exchanger for melting located outside the Third Region is preferred in the case of especially sensitive substances, the surface temperature of the heat transfer surfaces of the heat exchanger for melting being preferably max. about 5° C., preferably max. about 3° C. and especially max. about 1.5° C., above the melting point of the target product.

The flow resistance is so constructed and arranged that it firstly compacts the solid constituents present in the wash material, preferably the crystals of a suspension, without the crystals blocking the cause of compaction in the flow resistance. As a result, it is not necessary to use a movable scraper or rake which has to break up the compacted solids of wash material for entry into the Third Region. That breaking up is performed, in accordance with the invention, by the flow resistance.

According to an embodiment of the washing apparatus according to the invention, preference is given to the flow resistance being characterised by a relative free cross-sectional area in the range from 0 to about 100%, preferably in the range from about 20 to about 80%, and especially in the range from about 40 to about 60%, relative to the total area of the flow resistance.

Furthermore, it is preferred that openings provided in the flow resistance have a cross-section in the range from about 0,001 to about 50 mm, preferably in the range from about 5 to about 25 mm and more preferably in the range from about 10 to about 20 mm.

It is preferred that in the washing apparatus according to the invention the cross-section of the at least one opening is variable.

Furthermore, it is preferred that the walls of the openings are wettable with a liquid in order to improve the through flow capability of the wash material. For that purpose, a film is formed on the walls of the opening in order to wet said walls and to reduce or even to prevent the adhesion of the crystals. That film preferably consists mainly of melted target product, which is melted by means of a heating apparatus provided in the flow resistance.

These measures make it possible, for example, to balance out pressure fluctuations in the wash material, especially in the crystal bed, and to prevent the formation of blockages.

In accordance with an embodiment, the openings are provided with an adjustable orifice. According to another embodiment, the variability of the cross-section of the opening is brought about by means of the fact that the flow resistance consists of a first plate having openings and a further, second plate likewise having openings and arranged so that it can rotate in relation to the first plate.

According to a further embodiment, the at least one opening of the flow resistance can be formed by struts of a grid. The power of the flow resistance can be varied by means of the fact that at least two such grids are so arranged as to be movable with respect to one another and, as a result of relative displacement, the openings formed in the grids are covered over to a greater or lesser degree by struts of the respective other grid.

Furthermore, it is preferred that in the washing apparatus according to the invention the liquid phase of the wash material, for example melted crystals, exit from the at least one hole in the flow resistance in a crystal suspension forming the wash material. By that means, blockage of the openings provided in the flow resistance may be prevented and the separation performance of the washing column increased. The holes are preferably smaller than the average crystal diameter.

Furthermore, it is preferred that in an embodiment of the washing apparatus according to the invention, an A cross-section of the opening facing the Second Region is 10 times larger than the B cross-section facing the Third Region. Preferably, the openings are of conical construction. This measure also prevents blockage of the openings and, consequently, of the flow resistance. In addition, this measure facilitates the build-up of a crystal bed that is as uniform as possible. In this context, it is especially preferred that the surface of the flow resistance which faces the Second Region has convex recesses, from which the openings emanate.

Furthermore, it is preferred that in the washing apparatus according to the invention there is provided between the First Region and the Second Region a solid/liquid separation apparatus, preferably a filter, with a filtrate offtake line. Furthermore it is preferred that the concentration of the target product in the filtrate offtake line is the same as, preferably less than, the concentration of the target product in the liquid phase in the First Region. In addition, it is preferred that the concentration of the target product in the Third Region is greater than in the Second Region.

As suitable filters there may be used those filter materials that have a pore size which is smaller than the average particle size of the solid constituents present in the wash material. It is preferred that the average pore size of the filter materials is in the range from about 1 to about 1000 µm, preferably in the range from about 50 to about 800 µm and more preferably in the range from about 100 to about 500 µm. Suitable filter materials are among others wire grids, wire mesh, non woven wire, knitted wire.

It is preferred that in the washing apparatus according to the invention, the filter is formed in a wall adjacent to the Second Region. In addition, it is preferred that the wall in which the filter is constructed is arranged in the washing apparatus at an angle α in the range from 0 to less than about 90°, preferably from about 1 to about 50° or preferably from about 15 to about 60° and more preferably from about 10 to about 30° or from about 5 to about 15°, relative to the axis formed by the direction of flow of the wash material flowing through the washing apparatus.

In addition, it is preferred that at least the Second Region of the washing apparatus according to the invention, preferably the filter, is temperature-modifiable.

Furthermore, the invention relates to a purification apparatus comprising a crystal-producer connected by crystal-carrying means to the First Region of the washing apparatus defined herein before. As crystal-producer there comes into consideration, in principle, any apparatus that the person skilled in the art considers suitable for producing a crystal suspension. In this context, by way of example there may be mentioned cool disc crystallisers.

Furthermore, the invention relates to a purification apparatus comprising a crystal producer that is connected in a crystal carrying way with the First Region of a washing apparatus, comprising
- a First Region, to which a wash material is supplied,
- a Second Region, in which the wash material is washed, and
- a Third Region, in which the wash material is melted, and also
- a flow resistance provided between the Second Region and the the Third Region, or the washing apparatus according to the invention.

According to a preferred embodiment of the purification apparatus according to the invention, there can be provided, between the crystal-producer and the washing apparatus, a dwell-time container, for example for maturation or homogenisation of the crystal suspension.

According to another embodiment of the purification apparatus according to the invention, there is provided an at least partial return, to the crystal suspension, of the mother liquor separated off by means of the filter. This may take place before or after, preferably after, the conveying apparatus, and especially preferred between the conveying apparatus and solid/liquid separation.

According to a further embodiment of the purification apparatus according to the invention, it comprises an at least partial return, to the Third Region, of the pure product melted in the Third Region.

In addition, another embodiment of the purification apparatus according to the invention comprises an at least partial return, into the flow resistance, of the pure product melted in the Third Region.

Furthermore, a further embodiment of the purification apparatus according to the invention comprises an at least partial return, to the Third Region, of the pure product melted in the Third Region, wherein swirling up of the crystals present in the Third Region is produced.

The main flows and returns provided in the purification apparatus and also the varying of the openings of the flow resistance can be controlled on the basis of data obtained at least one location by means of a preferably integral multi-thermosensor or multiple resistance thermometer. Preferably, the multi-thermosensor is arranged in the central region of the crystal bed, which is preferably rotationally symmetrical. This control serves the purpose of obtaining a wash material flow that is as uniform as possible and a separation performance that is as high as possible. This is accomplished especially by means of the main flows and returns being controlled on the basis of the temperature measurement, by which means it is possible to govern the position of the washing front. Moreover, the pressure conditions in the washing column can so be controlled. Details in this respect are to be found in DE 100 39 025 A1, DE 100 36 880 A1 and in DE 100 36 881 A1. The non-homogeneities in the crystal bed caused by a plurality of measurement probes are, as a result, avoided by ensuring control of the position of the washing front.

Furthermore, in accordance with the present invention it is preferred that at least two purification apparatuses according to the invention are arranged connected in series or in parallel to one another. The nature of the connected arrangement and the number of purification apparatuses or washing apparatuses used therein are governed by the purification requirements and the purification potential of the target product.

In addition, the present invention relates to a synthesis apparatus comprising a synthesis device, preferably a reactor, and a previously defined purification apparatus. In connection with the synthesis of acrylic acid and methacrylic acid and the preferred combinations of crystal-producers and washing apparatuses, reference is made to the statements in WO 02/055469. In an embodiment according to the invention it is thus preferred that the synthesis apparatus is a gaseous phase oxidation synthesis unit. In connection with the production of polymerizable materials, in particular the monomers acrolein, (meth)acrylic acid, in particular acrylic acid, reference is made to "Acrolein and derivatives" in "Stets geforscht", volume 1 and 2, Chemieforschung im Degussa Forschungszentrum Wolfgang 1988, pages 108 to 126.

Furthermore, the invention relates to a method of purifying a wash material, wherein the wash material is supplied by way of the First Region of a previously defined washing apparatus.

In a preferred embodiment of the method according to the invention, the wash material comprises at least about 20% by weight, preferably at least about 50% by weight and especially at least about 85% by weight, of the target product, preferably acrylic acid.

In addition, the invention relates to the use of the target product, obtainable according to a method according to the invention, in the production of food, polymers, fuels, lubricants, cleaning agents, dyes or pharmaceuticals.

Finally, the invention relates to the use of a washing apparatus according to the invention or of a purification apparatus according to the invention in the purification of target products such as food, monomers, fuels or solvents; or in wastewater treatment; or in isomer separation.

As foods, drinks are preferred. As monomers, acrylic acid, methacrylic acid, styrene, methyl methacrylate, butyl acrylate, benzoic acid, bisphenol A, caprolactam, fatty acids, monochloroacetic acid, methyl diisocyanate, toluylene diisocyanate, naphthalene, paraffin, p-, o- or m-dichlorobenzene, p-xylene, phthalide or derivatives of each of those or salts of each of those are preferred. As fuels, hydrazine or diesel is preferred.

The invention will be explained in greater detail herein below with reference to non-limiting Figures:

FIG. 1 shows a washing apparatus consisting of a First Region 1, which can be provided with a conveying means 61, preferably a conveying spiral, a Second Region 2 and a Third Region 3. Between the Second Region 2 containing the wash material 4 and the Third Region 3, there is provided a flow resistance 6, which is fixed. This flow resistance is in the form of a baffle having openings 10. The flow resistance furthermore has product flow returns 26, by means of which the melted target product is introduced into the flow resistance 6 and can exit from the openings 10. The flow resistance furthermore has a hole 31 for accommodating a multi-thermosensor 29 having various measurement locations 30. The Second Region 2 forms a washing column 53. The washing column 53 is preferably in the form of a rotationally symmetrical pipe, through which, in the same manner as the Second Region 2, a central longitudinal axis 5 of the Second Region 2 passes. The walls of the washing column 53 have a surface that is as smooth as possible. The washing column 53 contains the crystal bed 32, which flows through the washing column 53 in the direction of the straight arrow. Contrary to the direction of flow of the crystal bed 32, a washing liquid 33 flows through the crystal bed in accordance with the direction of the snaking arrow. Between the First Region 1 and the Second Region 2 there is arranged a filter 7, which is provided with a filter offtake line 8. A wall 9 of the filter 7 is adjacent to the wall of the washing column 53. That wall of the filter 7 which faces the wash material 4 is in the form of a conical perforated plate having a sieve, the wall of the filter 7 being arranged at an angle α from at least 0 to less than about 90° to the central longitudinal axis of the Second Region 5. The washing column 53 accordingly terminates at one end in the flow resistance 6 and at the other end, except for the remaining opening to the First Region for a wash material supply 52, in the filter 7. The First Region 1 has the wash material supply 52, in the form of a pipe, in which the multi-thermosensor 29 is fixed by means of a tripod 28. The Third Region 3 has a melting apparatus 54, into which there opens out a product circuit melt return and from which a product circuit suspension return leaves. On the one hand, the washing apparatus described in this paragraph can be operated so that the First Region 1 is arranged at the bottom, as shown in FIG. 1. However, it is also possible to operate the washing apparatus contrariwise, in that the wash material is charged from above via the First Region 1.

Figure 2:
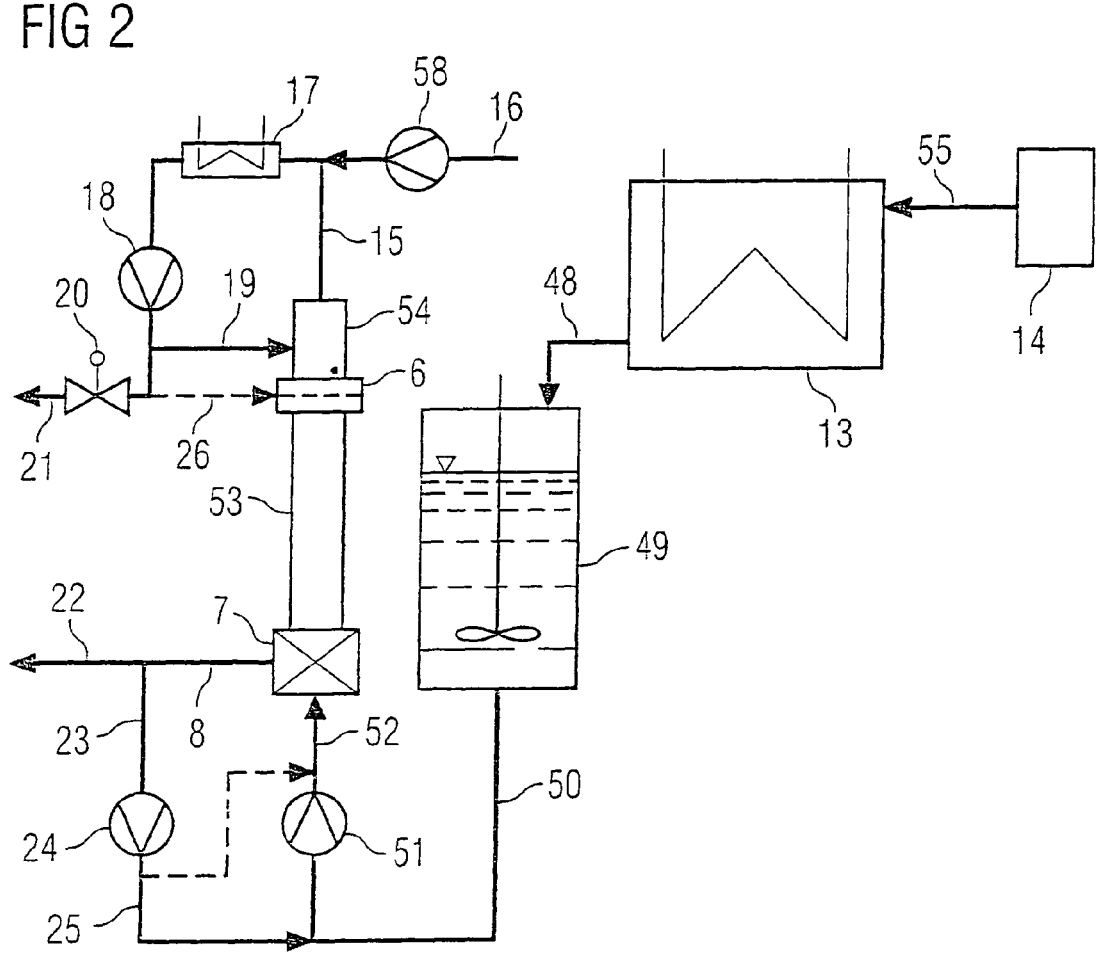
FIG. 2 shows, in diagrammatic form, the structure of a purification apparatus according to the present invention.

In FIG. 2, a feed produced in a reactor, with an optionally interposed quenching apparatus, is supplied, by way of a feed line 55, to a crystal-producer 13, in which the wash material is produced in the form of a crystal suspension. By way of a crystal overflow 48, the crystal suspension is transferred to a dwell-time container 49 and, by way of a dwell-time container overflow 50, is supplied to a conveying device 51 for wash material/suspension. By way of a wash material supply 52, the crystal suspension passes along the filter 7 into the washing column 53 and, by way of the flow resistance 6, into the melting apparatus 54, which is followed by the product circuit suspension return 15, which opens out into a heat exchanger 17 and, by way of a product circuit pump 18, returns by way of the product circuit melt return 19 into the melting apparatus 54 or by way of the product flow return 26 into the flow resistance 6. The amount of target product returned is governed by means of a pressure valve 20 controlling the product outlet. The pressure valve 20 is controlled via the multi-thermo-element 30 by means of multi-point regulation so as to regulate the height of the washing front in the washing column by varying the amount of retained and consequently returned target product. The purified target product leaves the purification apparatus by way of a pure-product outlet 21. The pure-product outlet 21 may be followed by a further purification apparatus, the pure product that leaves the pure-product outlet 21 first being passed into a further crystal-producer, which is followed by the further constituents of the purification apparatus shown in FIG. 2 or at least part thereof being returned to the original crystal-producer 13, or both. Part of the filtrate 22 can be supplied to the wash material by being passed into the dwell-time container overflow 50, by way of a first filtrate return 23 operated by a filtrate return pump 24, through a second filtrate return 25. In respect of preferred connected arrangements of a plurality of purification apparatuses according to the invention, reference is made to WO 02/055469. In addition, at least part of the filtrate 22 can be supplied to the delivery side of the conveying device 51 in accordance with the conduit shown by the broken line. This measure permits the adjustment of the conveying flow of the wash material or of the suspension respectively, irrespective of the total mass flow. Furthermore, upstream of the product circuit heat exchanger 17, inhibitor supplied through an inhibitor supply 16 can be added to the target product by means of an inhibitor metering device 58. This is always recommended when the target product is already so pure that, by virtue of its purity, it has a tendency to undesirable and spontaneous reactions. Furthermore, melting of the crystals comprising the target product can be carried out by moving a target-product-comprising melt in the circuit formed by the reference numerals 15, 17, 18 and 19.

Figure 3:
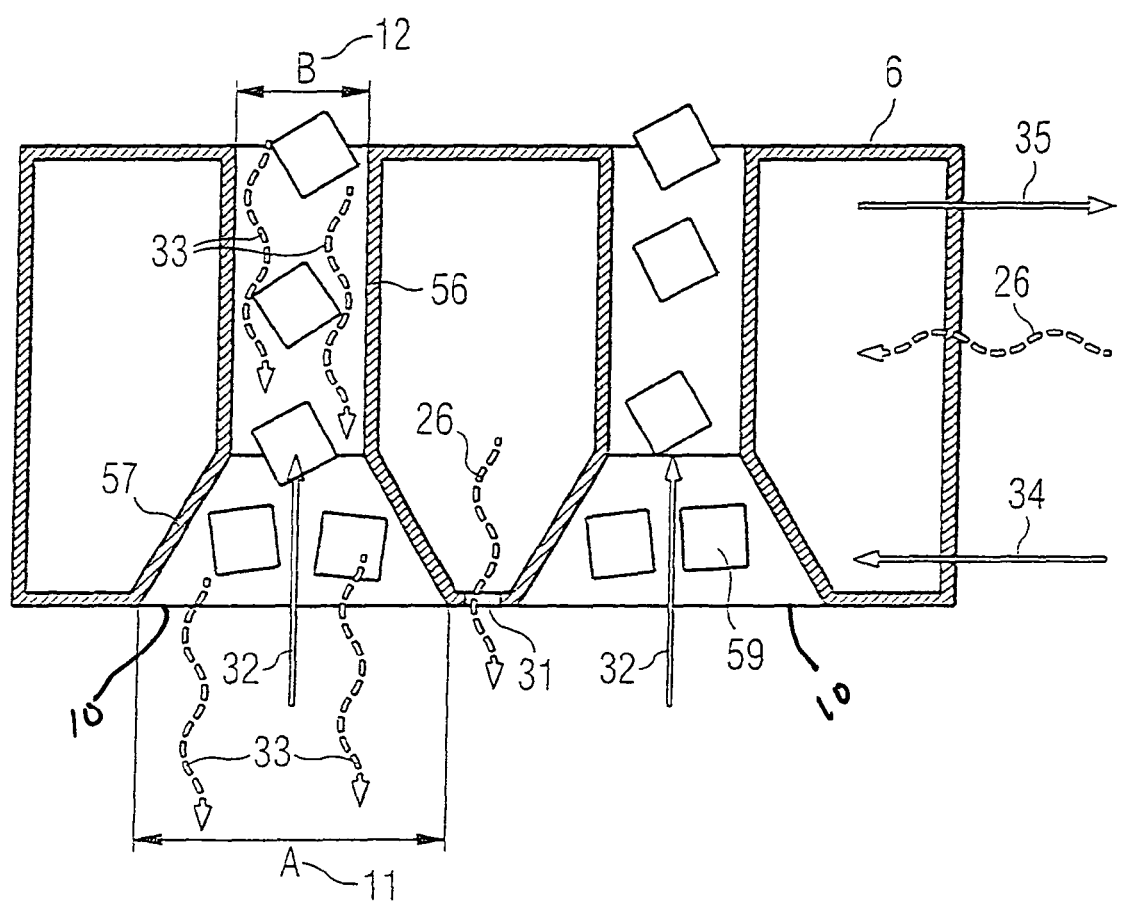
FIG. 3 is a cross-section, in diagrammatic form, through a flow resistance according to the present invention having the form of a baffle.

FIG. 3 shows a flow resistance 6 in the form of a baffle. The baffle has, in the plane shown, two openings 10, an A cross-section 11 of the openings 10 facing the Second Region 2 being larger than a B cross-section 12 facing the Third Region 3. Starting as seen from the Second Region 2, the opening 10 first has a conical hole 57 having the A cross-section 11 at one end and the B cross-section 12 at the other end. Following on from the B cross-section 12 of the conical hole 57 is a parallel hole 56 having the B cross-section 12. The crystals 59 of the crystal bed 32 move along the direction of the straight arrows through the openings 10. The washing liquid 33 flows in the opposite direction, in the direction of the snaking arrows. For heating of the flow resistance in the form of a baffle, it comprises a temperature-modifying medium inlet 34 and a temperature-modifying medium outlet 35. Furthermore, products reach, by way of the product flow return 26, the openings 10 and that side of the flow resistance 6 in the form of a baffle that faces the Second Region 2. The target-product-comprising melt returned to the flow resistance 6 by way of the product flow return 21 is supplied to the crystals 59, for the purpose of washing them, by way of the hole 31. In addition, the multi-thermo-element 30 can be passed through the hole 31.

Figure 4:
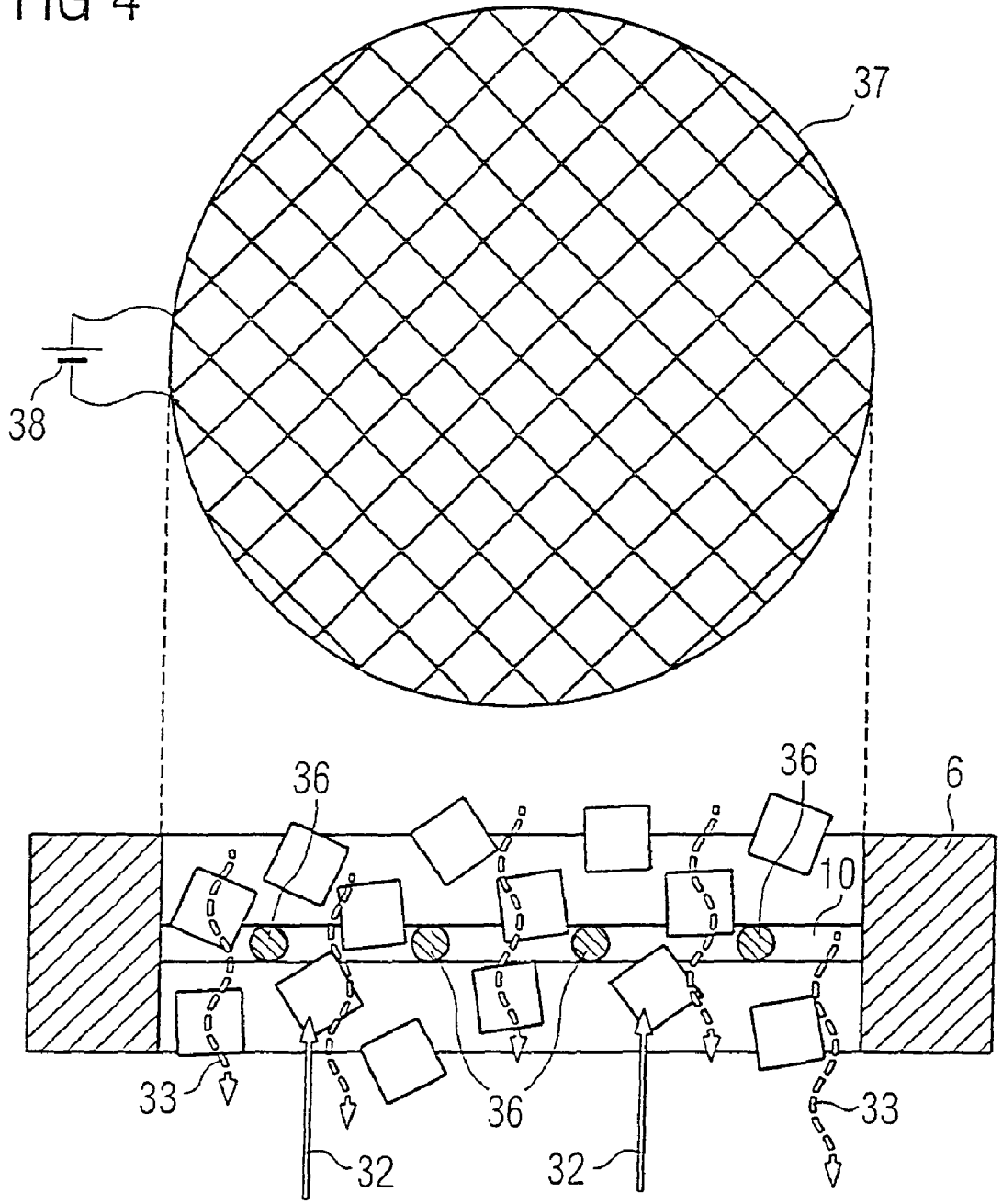
FIG. 4 shows, in diagrammatic form, a grid as a flow resistance according to the present invention, in cross-section and in a partial top view.

FIG. 4 shows a flow resistance 6 in the form of a grid, wherein the openings 10 are formed by the struts 36. The grid 37 is heatable by means of a heating device 38. In a further development the struts 36 are part of a lattice. It is preferred, in the developments described in this paragraph that the struts 36 are of a hollow shape and that a heating/cooling agent is guided through the hollow space being formed, to ensure a heating, which is preferably free from overheating of the crystals to be melted. Owing to the embodiments shown in this paragraph the flow resistance 6 can be heated. Reference is made, with respect to the further reference numerals, to the statements made regarding the previous Figures.

Figure 5:
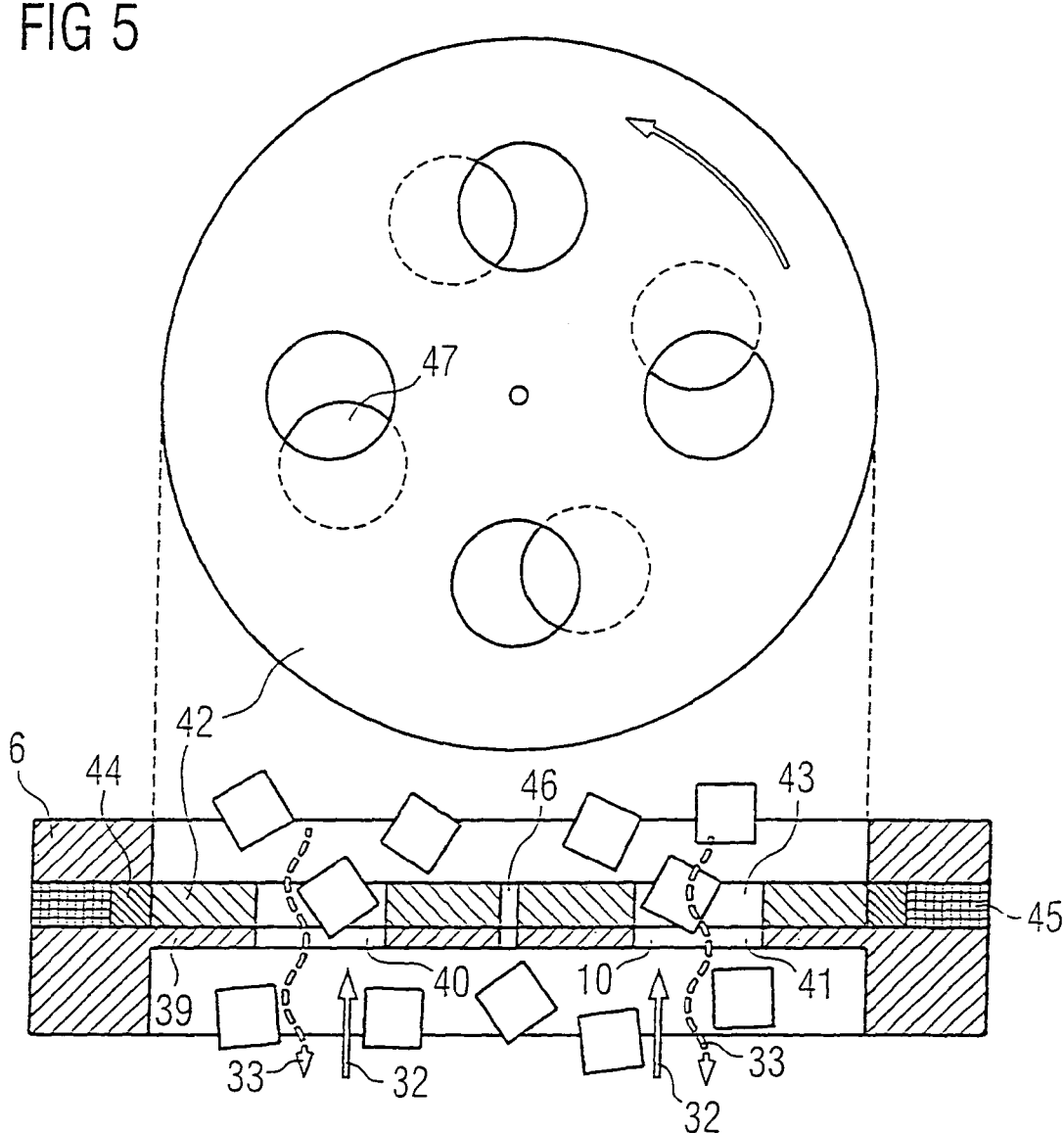
FIG. 5 is a diagrammatic drawing of a baffle having adjustable opening cross-sections as a flow resistance according to the present invention, in cross-section and in a partial top view.

FIG. 5 shows a flow resistance 6 having openings 10 of variable cross-section, comprising a fixed lower perforated plate 39 and a perforated plate 42, rotatable with respect to the lower perforated plate 39, which perforated plate 42 can be moved about a multi-thermosensor guideway 46 by means of a ring magnet 44 having a drive coil 45. Reference is made, with respect to the further reference numerals, to the statements made regarding the previous Figures.

Figure 6:
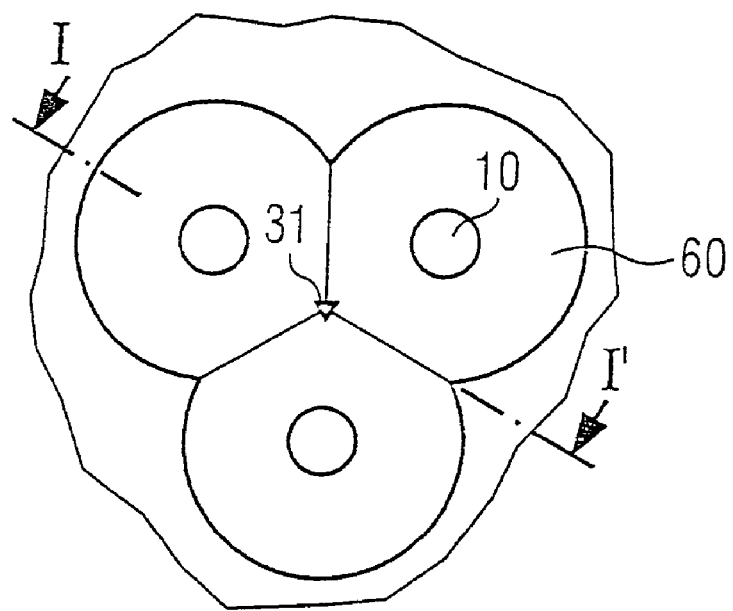
FIG. 6 shows a flow resistance 6 in a top view.

FIG. 6 shows a flow resistance in a top view. This flow resistance has a plurality of holes 10, each of which has a conical hole of convex construction. Furthermore, this portion of the flow resistance has a hole 31.

Figure 7:
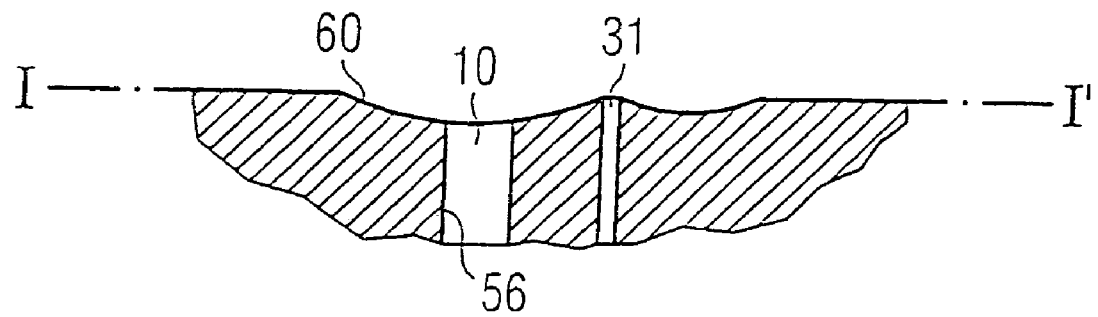
FIG. 7 is a diagrammatic drawing of the baffle cross-section along the axis I/I' of the drawing in FIG. 6.

FIG. 7 is a cross-section along the axis I/I' of the portion of flow resistance shown in FIG. 6. This flow resistance has openings 10 and 31. The opening 10 is formed from a convex hole 60 and a parallel hole 56, which are constructed substantially at right angles to the surface of the portion of flow resistance.

Furthermore, the invention will be explained in greater detail herein below by non-limiting Examples.

EXAMPLES

Example 1

Water Treatment

In an apparatus according to FIG. 2, having a 100-litre cool disc crystalliser from the company GMF-Gouda B.V. as crystal-producer 13, a 10% by weight acetic acid/water mixture was introduced into the crystalliser. Heat of crystallisation was drawn off by way of the cooling surfaces of the cool disc crystalliser. The equilibrium temperature of the mixture used was 3.5° C. The suspension produced on crystallisation (suspension density about 30% by weight, corresponding to a crystallisation temperature of minus 3.5° C.) was continuously supplied, by way of the dwell-time container 49, to a washing apparatus according to FIG. 1 (internal diameter 82 mm, length 550 mm) comprising a conical filter 7 (filter material 1.4571 with a mesh size of 250 µm, lower diameter 27.7 mm, upper diameter 80.5 mm) and a flow resistance according to FIG. 3 (height 60 mm with 9 through-holes each of 14 mm) using an eccentric helical pump (150 litres/hour max. delivery performance) from the company Netzsch GmbH.

In order to produce the contraflow wash, about 20% by weight of the total volumetric flow was taken off by way of the pure-product outlet 21, so that some of the crystals of the upwardly moving crystal bed, after having been melted, flowed back down through the crystal bed. By that means, the concentration of acetic acid at the head of the washing column could be reduced to 2.8% by weight.

Example 2

An acrylic acid mixture having the composition given in Table 1 was introduced into an apparatus according to FIG. 2 having a 100-litre cool disc crystalliser (GMF-Gouda B.V.):

TABLE 1

| Name | | Feed |
|---|---|---|
| water | % | 8.0 |
| acetic acid | % | 0.052 |
| furfural | % | 0.006 |
| benzaldehyde | % | 0.007 |
| acrolein | % | <0.0001 |
| propionic acid | % | 0.028 |
| protoanemonin | % | 0.006 |
| acrylic acid | % | 91.625 |
| MEHQ | % | 0.016 |
| HQ | % | 0.017 |
| PZ | % | 0.036 |
| D-acrylic acid | % | 0.227 |
| MA | % | 0.030 |
| others | % | 0.059 |

MEHQ: methyl ethyl hydroquinone
HQ: hydroquinone
PZ: phenothiazine
D-acrylic acid: dimeric acrylic acid
MA: maleic anhydride The heat of crystallisation was drawn off by way of the cooling surfaces of the cool disc crystalliser. The equilibrium temperature of the mixture used was 5° C. The suspension produced on crystallisation (suspension density about 20% by weight, corresponding to a crystallisation temperature of 2° C.) was continuously supplied, by way of the dwell-time container, to the washing column according to FIG. 1 (internal diameter 82 mm, length 520 mm) comprising a conical filter (filter material 1.4571 with a mesh size of 250 µm, lower diameter 27.7 mm, upper diameter 80.5 mm) and a flow resistance according to FIG. 4 (wire strut thickness 0.5 mm, mesh size 1.5 mm) using an eccentric helical pump (300 litres/hour max. delivery performance) from the company Netzsch GmbH.

In order to produce the contraflow wash, the pure-product outlet 21 was completely closed off, so that all of the crystals of the upwardly moving crystal bed, after having been melted, flowed back down through the crystal bed. By that means, after 24 hours, a pure acrylic acid having a composition according to Table 2 was obtained at the head of the washing column.

TABLE 2

| Name | | Product |
|---|---|---|
| water | % | 1.37 |
| acetic acid | % | 0.013 |
| furfural | % | <0.0001 |
| benzaldehyde | % | 0.001 |
| propionic acid | % | 0.01 |
| protoanemonin | % | 0.001 |
| acrylic acid | % | 98.558 |
| MEHQ | % | 0.001 |
| HQ | % | n.d. |
| PZ | % | n.d. |
| D-acrylic acid | % | 0.03 |
| MA | % | <0.001 |
| others | % | 0.009 |

MEHQ: methyl ethyl hydroquinone
HQ: hydroquinone
PZ: phenothiazine
D-acrylic acid: dimeric acrylic acid
MA: maleic anhydride
n.d. below the measurement limits Table 2 shows that the washing apparatus according to the invention can be successfully used for purifying acrylic acid to high levels of purity. The filtrate obtained in the course of that purification had a composition according to Table 3.

TABLE 3

| Name | | Filtrate |
|---|---|---|
| water | % | 10.3 |
| acetic acid | % | 0.06 |
| furfural | % | 0.007 |
| benzaldehyde | % | 0.008 |
| propionic acid | % | 0.03 |
| protoanemonin | % | 0.005 |
| acrylic acid | % | 89.104 |
| MEHQ | % | 0.018 |
| HQ | % | 0.022 |
| PZ | % | 0.042 |
| D-acrylic acid | % | 0.342 |
| MA | % | 0.09 |
| others | % | 0.053 |

MEHQ: methyl ethyl hydroquinone
HQ: hydroquinone
PZ: phenothiazine
D-acrylic acid: dimeric acrylic acid
MA: maleic anhydride The concentration figures were determined by means of gas chromatography. Water concentrations were determined in accordance with ASTM D 1364 and the inhibitor concentrations were determined in accordance with ASTM D 3125.

Example 2 shows considerable purification as a result of the apparatus according to the invention used in the method according to the invention. Comparison of Tables 1 and 2 shows that, with the exception of the target product acrylic acid, it was possible to reduce the concentrations of all further impurities.

LIST OF REFERENCE NUMERALS

| 1. | First Region |
|---|---|
| 2 | Second Region or column 2a, respectively |
| 3 | Third Region |
| 4 | Wash material |
| 5 | Central longitudinal axis of the Second Region |
| 6 | Flow resistance |
| 7 | Filter |
| 8 | Filter offtake line |
| 9 | Wall |
| 10 | Opening |
| 11 | A cross-section |
| 12 | B cross-section |
| 13 | Crystal-producer |
| 14 | Synthesis device |
| 15 | Product circuit suspension return |
| 16 | Inhibitor supply |
| 17 | Product circuit heat exchanger |
| 18 | Product circuit pump |
| 19 | Product circuit melt return |
| 20 | Pressure control valve-product outlet |
| 21 | Pure-product outlet |
| 22 | Filtrate |
| 23 | First filtrate return |
| 24 | Filtrate return pump |
| 25 | Second filtrate return |
| 26 | Product flow return |
| 27 | Conical perforated plate with sieve |
| 28 | Tripod |
| 29 | Multi-thermosensor |
| 30 | Multi-thermo-element or multiple resistance thermometer |
| 31 | Hole |
| 32 | Crystal bed |
| 33 | Washing liquid |
| 34 | Temperature-modifying medium inlet |
| 35 | Temperature-modifying medium outlet |
| 36 | Struts |
| 37 | Grids of various mesh sizes |
| 38 | Heating device |
| 39 | Lower perforated plate |
| 40 | Openings, lower perforated plate |
| 41 | Chamfer of opening |
| 42 | Upper perforated plate |
| 43 | Openings, upper perforated plate |
| 44 | Ring magnet |
| 45 | Drive coil |
| 46 | Multi-thermosensor guideway |
| 47 | Free cross-sectional surfaces |
| 48 | Crystal overflow |
| 49 | Dwell-time container |
| 50 | Dwell-time container overflow |
| 51 | Conveying device for wash material/suspension |
| 52 | Wash material supply |
| 53 | Washing column |
| 54 | Melting apparatus |
| 55 | Feed line |
| 56 | Parallel hole |
| 57 | Conical hole |
| 58 | Inhibitor metering device |
| 59 | Crystals |
| 60 | Convex hole |
| 61 | Conveying means or conveying spiral, respectively |

What is claimed is:

1. A washing apparatus comprising:
a material conveying means comprising an outlet and a connection to a First Region wherein the material conveying means, which is free of pulsation, is located outside of the washing apparatus and supplies a wash material to the First Region;
wherein said conveying means comprises a spiral conveyor pump;
a First Region, to which the wash material is supplied,
a Second Region, in which the wash material is washed,
a solid/liquid separation apparatus with a filtrate offtake line located between the First Region and the Second Region,
a Third Region, in which the wash material is melted wherein the Third Region comprises a melting apparatus,
a heat exchanger in communication with said Third Region, wherein said heat exchanger is located outside of said Third Region, and
a flow resistance is arranged in a stationary position between the Second Region and the Third Region and is non-rotatable about a central longitudinal axis of the Second Region, wherein the flow resistance comprises multiple variable openings wherein each opening includes an "A" cross-section facing the Second Region and a "B" cross-section facing the Third Region; and
a multi-thermosensor positioned to extend through the First Region, the a solid/liquid separation apparatus, the Second Region, the flow resistance and the Third Region wherein the multi-thermosensor has at least one measurement location and controls varying the size of the variable openings of the flow resistence on the basis of data obtained at least one location of the washing apparatus.

2. The washing apparatus according to claim 1, wherein the "A" cross-section facing the Second Region is at least 10 times larger than the "B" cross-section facing the Third Region.

3. The washing apparatus according to claim 1, wherein the solid/liquid separation apparatus is in the form of a filter in a wall adjacent to the Second Region.

4. The washing apparatus according to claim 3, wherein the wall is arranged at an angle α in the range from 0 to less than about 90°, relative to the central longitudinal axis.

5. The washing apparatus according to claim 1, wherein the flow resistance is characterized by a relative free cross-sectional area in the range from 0 to less than about 100%, relative to the total area of the flow resistance.

6. The washing apparatus according to claim 1, wherein the multi-thermosensor is located in the central area of the washing apparatus.

7. The washing apparatus according to claim 1, wherein the flow resistance further comprises a multi-thermosensor guideway opening for the multi-thermosensor to pass through, a fixed lower perforated plate and an upper perforated plate rotatable with respect to the lower perforated plate wherein the upper perforated plate is rotated by input from the multi-thermosensor.

8. A purification apparatus comprising a crystal-producer that is connected in a crystal-carrying way with the First Region of a washing apparatus, said purification apparatus comprising:
a material conveying means comprising an outlet and a connection to a First Region wherein the material conveying means is located outside of the washing apparatus and supplies a wash material free of pulsation to the First Region; wherein said conveying means comprises a spiral conveyor pump;
a First Region, to which the wash material is supplied,
a Second Region, in which the wash material is washed,
a Third Region, in which the wash material is melted,
a heat exchanger in communication with said Third Region, wherein said heat exchanger is located outside of said Third Region, and
a flow resistance, for compacting the wash material without the wash material blocking the flow resistance; wherein the flow resistance is arranged in a stationary position between the Second Region and the Third Region wherein the flow resistance comprises multiple variable openings wherein each opening includes an "A" cross-section facing the Second Region and a "B" cross-section facing the Third Region; and
a multi-thermosensor positioned to extend through the First Region, the a solid/liquid separation apparatus, the Second Region, the flow resistance and the Third Region wherein the multi-thermosensor has at least one measurement location and controls the varying of size of the variable openings of the flow resistance on the basis of data obtained at least one location of the washing apparatus.

9. The purification apparatus according to claim 8, wherein the multi-thermosensor is located in the central area of the washing apparatus.

10. The purification apparatus according to claim 8 further comprising a multi-thermosensor guideway opening for the multi-thermosensor to pass through and the flow resistance comprises a fixed lower perforated plate and an upper perforated plate rotatable with respect to the lower perforated plate wherein the upper perforated plate is moved about the multi-thermosensor.

11. The purification apparatus according to claim 10, wherein the flow resistance comprises a ring magnet and a drive coil to rotate the upper perforated plate.

12. The washing apparatus according to claim 1, wherein the wash material is a crystal suspension comprising acrylic acid wherein the concentration of the acrylic acid in the crystals is at least about 90% by weight.

13. The washing apparatus according to claim 12, wherein the crystal suspension consists of crystals or a liquid phase.

14. The purification apparatus according to claim 8, wherein the wash material is a crystal suspension comprising acrylic acid wherein the concentration of the acrylic acid in the crystals is at least about 90% by weight.

15. The washing apparatus according to claim 1, wherein the wash material comprises an acrylic acid mixture.

16. An apparatus for the purification of acrylic acid comprising:
a material conveying means comprising an outlet and a connection to a First Region wherein the material conveying means is located outside of the washing apparatus and supplies a wash material free of pulsation to the First Region; wherein said conveying means comprises a spiral conveyor pump;
a First Region, to which the wash material is supplied,
a Second Region, in which the wash material is washed,
a Third Region, in which the wash material is melted wherein the Third Region comprises a melting apparatus,
a heat exchanger in communication with said Third Region, wherein said heat exchanger is located outside of said Third Region, and
a flow resistance is arranged in a stationary position between the Second Region and the Third Region and is non-rotatable about a central longitudinal axis of the Second Region, wherein the flow resistance comprises multiple variable openings wherein each opening includes an "A" cross-section facing the Second Region and a "B" cross-section facing the Third Region; and
a multi-thermosensor positioned to extend through the First Region, the a solid/liquid separation apparatus, the Second Region, the flow resistance and the Third Region wherein the multi-thermosensor has at least one measurement location and controls the varying of the openings of the flow resistance on the basis of data obtained at least one location of the washing apparatus.

17. The washing apparatus of claim 16, wherein said multi-thermosensor is located in the central area of the washing apparatus.

18. The washing apparatus of claim 16, wherein said flow resistance further comprises a multi-thermosensor guideway opening for the multi-thermosensor to pass through and the flow resistance comprises a fixed lower perforated plate and an upper perforated plate rotatable with respect to the lower perforated plate wherein the upper perforated plate is moved about the multi-thermosensor.

19. The washing apparatus of claim 1, wherein said melting apparatus is located on the wall of the Third Region, within the Third Region, or a combination thereof.

20. A washing apparatus comprising:
a First Region, to which the wash material is supplied,
a Second Region, in which the wash material is washed,
a solid/liquid separation apparatus with a filtrate offtake line located between the First Region and the Second Region,
a Third Region, in which the wash material is melted wherein the Third Region comprises a melting apparatus ,and
a flow resistance is arranged in a stationary position between the Second Region and the Third Region and is non-rotatable about a central longitudinal axis of the Second Region, wherein the flow resistance comprises multiple variable openings wherein each opening includes an "A" cross-section facing the Second Region and a "B" cross-section facing the Third Region; and
a multi-thermosensor positioned to extend through the First Region, the a solid/liquid separation apparatus, the Second Region, the flow resistance and the Third Region wherein the multi-thermosensor has at least one measurement location in the washing apparatus and controls the varying of the openings of the flow resistence on the basis of data obtained at least one location of the washing apparatus.

21. The washing apparatus according to claim 1, wherein the "A" cross-section facing the Second Region is at least 10 times larger than the "B" cross-section facing the Third Region.

22. The washing apparatus according to claim 20 wherein the solid/liquid separation apparatus is in the form of a filter in a wall adjacent to the Second Region.

23. The washing apparatus according to claim 22 wherein the wall is arranged at an angle α in the range from 0 to less than about 90°, relative to the central longitudinal axis.

24. The washing apparatus according to claim 20 wherein the flow resistence is characterized by a relative free cross-sectional area in the range from 0 to less than about 100%, relative to the total area of the flow resistence.

25. The washing apparatus according to claim 20 wherein the multi-thermosensor is located in the central area of the washing apparatus.

26. The washing apparatus according to claim 20 wherein the flow resistence further comprises a multi-thermosensor guideway opening for the multi-thermosensor to pass through and the flow resistence comprises a fixed lower perforated plate and an upper perforated plate rotatable with respect to the lower perforated plate wherein the upper perforated plate is moved about the multi-thermosensor.

27. The washing apparatus according to claim 20 further comprising a material conveying means comprising an outlet and a connection to a First Region wherein the material conveying means, which is free of pulsation, is located outside of the washing apparatus and supplies a wash material to the First Region; wherein said conveying means comprises a spiral conveyor pump.

28. The washing apparatus according to claim 20 wherein the flow resistence comprises a ring magnet and a drive coil to rotate the upper perforated plate.

* * * * *